United States Patent
Itaya et al.

(10) Patent No.: US 8,669,528 B2
(45) Date of Patent: Mar. 11, 2014

(54) FLAT PANEL DETECTOR

(75) Inventors: Keiko Itaya, Tokyo (JP); Takehiko Shoji, Tokyo (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 0 days.

(21) Appl. No.: 13/699,447

(22) PCT Filed: Mar. 15, 2011

(86) PCT No.: PCT/JP2011/056028
§ 371 (c)(1),
(2), (4) Date: Nov. 21, 2012

(87) PCT Pub. No.: WO2011/148700
PCT Pub. Date: Dec. 1, 2011

(65) Prior Publication Data
US 2013/0068953 A1    Mar. 21, 2013

(30) Foreign Application Priority Data
May 26, 2010  (JP) .................. 2010-120247

(51) Int. Cl.
*G01T 1/20* (2006.01)

(52) U.S. Cl.
CPC .................. *G01T 1/2018* (2013.01)
USPC ........................................ 250/368

(58) Field of Classification Search
CPC ....... G01T 1/2018; G21K 4/00; H01J 29/385; A61B 6/3208; A61B 6/4233; A61B 6/4488
USPC ........................................ 250/368
See application file for complete search history.

(56) References Cited

U.S. PATENT DOCUMENTS

| | | | | |
|---|---|---|---|---|
| 6,977,385 | B2 * | 12/2005 | Struye et al. | 250/484.4 |
| 7,026,632 | B2 * | 4/2006 | Leblans | 250/484.4 |
| 7,193,226 | B2 * | 3/2007 | den Bergh et al. | 250/484.4 |

FOREIGN PATENT DOCUMENTS

| | | |
|---|---|---|
| JP | 2000-009847 | 1/2000 |
| JP | 2002-333480 | 11/2002 |
| JP | 2006-058099 | 3/2006 |
| JP | 2008-051793 | 3/2008 |
| JP | 2009-002776 | 1/2009 |
| JP | 2009-300148 | 12/2009 |
| JP | 2009-300213 | 12/2009 |
| JP | 2010-060414 | 3/2010 |

* cited by examiner

*Primary Examiner* — Kiho Kim
(74) *Attorney, Agent, or Firm* — Lucas & Mercanti, LLP (57) ABSTRACT

A flat panel radiation detector is disclosed, comprising a scintillator panel provided on a support with a phosphor layer comprising columnar crystals and a protective layer sequentially in this order, and the scintillator panel being coupled with a planar light receiving element having plural picture elements which are arranged two-dimensionally, in which the difference between to average void fraction of an edge portion of the phosphor layer and the average void fraction of a base portion is not less than 5% and not more than 25%, and the void fraction decreases from the base portion to the edge portion. There is provided a flat panel radiation detector with a phosphor layer which exhibits enhanced physical resistance to shock and is superior in sharpness and emission efficiency.

16 Claims, 4 Drawing Sheets

FLAT PANEL DETECTOR

CROSS REFERENCE TO RELATED APPLICATION

This Application is a 371 of PCT/JP2011/056028 filed on Mar. 15, 2011 which, in turn, claimed the priority of Japanese Patent Application No. 2010-120247 filed on May 26, 2010, both applications are incorporated by reference herein.

TECHNICAL FIELD

The present invention relates to a flat panel detector for use in radiographic imaging and in particular to a compact flat panel detector with a smaller non-imaging area.

TECHNICAL BACKGROUND

There have been broadly employed radiographic images such as X-ray images for diagnosis of the conditions of patients in medical practice. Specifically, radiographic images using an intensifying-screen/film system have achieved enhancement of speed and image quality over its long history and are still used on the scene of medical treatment as an imaging system having high reliability and superior cost performance in combination. However, these image data are so-called analog image data, in which free image processing or instantaneous image transfer cannot be realized.

Recently, there appeared digital system radiographic image detection apparatuses, as typified by a computed radiography (also denoted simply as CR) and a flat panel RADIATION detector (also denoted simply as FPD). In these apparatuses, digital radiographic images are obtained directly and can be displayed on an image display apparatus such as a cathode tube or liquid crystal panels, which renders it unnecessary to form images on photographic film. Accordingly, digital system radiographic image detection apparatuses have resulted in reduced necessities of image formation by a silver salt photographic system and leading to drastic improvement in convenience for diagnosis in hospitals or medical clinics.

The computed radiography (CR) as one of the digital technologies for radiographic imaging has been accepted mainly at medical sites. However, image sharpness is insufficient and spatial resolution is also insufficient, which have not yet reached the image quality level of the conventional screen/film system. Further, there appeared, as a digital X-ray imaging technology, an X-ray flat panel detector (FPD) using a thin film transistor (TFT), as described in, for example, the article "Amorphous Semiconductor Usher in Digital X-ray Imaging" described in Physics Today, November, 1997, page 24 and also in the article "Development of a High Resolution, Active Matrix, Flat-Panel Imager with Enhanced Fill Factor" described in SPIE, vol. 32, page 2 (1997).

To convert radiation to visible light is employed a scintillator panel made of an X-ray phosphor which is emissive for radiation. The use of a scintillator panel exhibiting enhanced emission efficiency is necessary for enhancement of the SN ratio in radiography at a relatively low dose. Generally, the emission efficiency of a scintillator panel depends of the scintillator thickness and X-ray absorbance of the phosphor. A thicker phosphor layer causes more scattering of emission within the phosphor layer, leading to deteriorated sharpness. Accordingly, necessary sharpness for desired image quality level necessarily determines the layer thickness.

Specifically, cesium iodide (CsI) exhibits enhanced conversion efficiency of X-rays to visible light and can easily form a phosphor of a columnar crystal structure through vapor deposition, whereby scattering of emitted light within a crystal is inhibited through a light guide effect, rendering it feasible to increase the thickness of a phosphor layer. However, the CsI alone exhibits lowered emission efficiency, so that a mixture of CsI and sodium iodide (NaI) at an appropriate ratio is deposited on a support in the form of a sodium activated cesium iodide (CsI:Na) through vapor deposition, as described in, for example, JP 54-035060 B. Alternatively, recently, a mixture of CsI and thallium iodide (TlI) at an appropriate ratio is deposited on a support in the form of a thallium activated cesium iodide (CsI:Tl) through vapor deposition, followed by annealing to achieve enhanced light conversion efficiency, which is employed as an X ray phosphor.

However, a need in the market is high and both emission efficiency and sharpness were not satisfied even by the foregoing methods.

To achieve an improvement of sharpness, there was disclosed a technique in which the thickness of a scintillator layer was increased to 500 μm or more and a filling factor of columnar crystals in the scintillator layer was controlled to 70 to 85% to achieve enhanced image resolution and high image quality (as described in, for example, Patent document 1), but such a technique was not sufficient to meet the need of the market.

PRIOR ART LITERATURE

Patent Document

Patent document 1: JP 2006-058099 A

SUMMARY OF THE INVENTION

Problems to be Solved

In view of the foregoing technical background, it is the first object of the invention to provide a flat panel detector exhibiting more enhanced emission efficiency and higher image quality.

In cases when increasing the void fraction of a scintillator layer to achieve enhanced sharpness, the scintillator layer is sometimes destroyed, giving rise to image defects when a shock was applied to a flat panel detector, so that it was necessary to take care in handling of the flat panel detector. Accordingly, it is the second of the invention to provide a flat panel detector which is difficult to form image defects caused by shock.

Means for Solving the Problems

The foregoing problems of the invention can be dissolved by the following constitution:

1. A flat panel detector comprising a scintillator panel which comprises a phosphor layer comprising columnar crystals and a protective layer sequentially provided on a support in this order, and the scintillates panel is coupled with the light receiving surface of a planar light receiving element having plural picture elements which are arranged two-dimensionally, wherein the difference of an average void fraction of a base portion of the phosphor layer minus an average void fraction of an edge portion is not less than 5% and not more than 25%, and a void fraction decreases from the base portion to the edge portion.

In cases in which a void fraction is uniform from the base portion to the edge portion, when the void fraction is increased to enhance sharpness, a columnar phosphor becomes thin or the number of phosphors per unit area decreases, and as a result, columnar crystals are easily broken by shock. On the other hand, a decrease of the void fraction to increase strength to impact results in lowering of sharpness. In the invention, it is assumed that the thickness of the base portion of the phosphor is reduced to less than that of the edge portion, whereby, even when the void fraction of the whole phosphor layer is the same to maintain sharpness, the strength of the edge portion of the phosphor layer to which a large power is applied when subjected to an impact is increased, making it resistant to destruction. It is also assumed that, in a conventional phosphor with a columnar structure having no inclination in void fraction, an X-ray irradiated to a void portion goes through the void portion without being exposed to the phosphor; on the contrary, the phosphor layer of the invention is low in the void fraction of the edge portion, so that the fraction of irradiation onto a phosphor crystal is high, resulting in enhanced availability of an X-ray and leading to enhanced luminance.

2. The flat panel detector, as described in the foregoing 1, wherein a change in void fraction of the base portion of the phosphor layer is not than 10% and not more than 25%.

Specifically, it is presumed that a large change in void fraction of the base portion broadens the distance between columnar crystals on the support side, rendering it feasible to reduce diffusion of light via a support and resulting in enhance sharpness, and meanwhile, void fractions of the center portion and the edge portion become less, resulting in further enhanced X-ray employment efficiency and leading to enhanced luminance.

3. The flat panel detector, as described in the foregoing 1 or 2, wherein the support contains carbon, aluminum or glass as a main component.

4. The flat panel detector, as described in the foregoing 3, wherein the thickness of the support is not less than 0.3 mm and not more than 1.0 mm.

5. The flat panel detector, as described in the foregoing 1 or 2, wherein the support is a resin.

6. The flat panel detector, as described in the foregoing 5, wherein the support comprises at least one of a polyimide (PI) and a polyethylene naphthalate (PEN).

7. The flat panel detector, as described in the foregoing 5 or 6, wherein the thickness of the support is not less than 0.05 mm and not more than 0.20 mm.

8. The flat panel detector, as described in any of the foregoing 1 to 7, wherein the protective layer is a laminated film and is not adhered to the phosphor layer.

9. The flat panel detector, as described in any of the foregoing 1 to 7, wherein the protective layer is a resin and is adhered to the phosphor layer.

10. The flat panel detector, as described in the foregoing 8, wherein the protective layer is a poly(p-xylylene) or a hot melt resin.

11. The flat panel detector, as described in any of the foregoing 1 to 10, wherein the scintillator panel is coupled with the light-receiving surface of the flat light-receiving element, while being pressed with an auxiliary material.

12. The flat panel detector, as described in any of the foregoing 1 to 10, wherein the scintillator panel is coupled with the light-receiving surface of the flat light-receiving element through a resin layer.

13. The flat panel detector, as described in any of the foregoing 1 to 12, wherein an FOP (fiber optic plate) is used for coupling of the scintillator panel and the flat light-receiving element.

14. The flat panel detector, as described in any of the foregoing 1 to 13, wherein the phosphor layer comprises CsI (cesium iodide).

15. The flat panel detector, as described in the foregoing 14, wherein the flat light-receiving element is a flat plate light receiving element provided with a thin film transistor (TFT) formed on a glass support.

16. The flat panel detector, as described in the foregoing 14, wherein the flat light-receiving element is a CCD or a CMOS.

Effect of the Invention

The foregoing means made it feasible to prepare a flat panel radiation detector provided with a phosphor layer capable of ensuring physical resistance to shock or the like, with enhanced sharpness and emission efficiency.

EMBODIMENTS OF THE INVENTION

In the following, there will be detailed the present invention and constituents thereof.

Constitution of Scintillator Panel:

The scintillator panel of the invention comprises on a support a phosphor layer comprising columnar crystals and a protective layer for the phosphor layer, and preferably, a sublayer is provided between the support and the phosphor layer. A reflection layer may be provided on the support and there may also be constitution of a reflection layer, a sublayer and a phosphor layer. There will be described below the individual constituent layers and constituent elements.

Phosphor Layer (Scintillator Layer):

The phosphor layer related to the invention features a phosphor layer comprised of columnar phosphor crystals. After completing vapor deposition, the formed phosphor is cut to a prescribed size and the entire surface of a support is a phosphor layer forming area.

A variety of commonly known phosphor materials can be used for a material to form a phosphor layer but cesium iodide (CsI) is preferable which exhibits a relatively high conversion factor of X-rays to visible light and can easily form, by a process of vapor deposition, a columnar crystal structure of a phosphor, which is capable of inhibiting scattering of emitted light within a crystal through an optical guiding effect and increasing the thickness of a phosphor layer.

However, CsI alone results in reduced emission efficiency, so that various activators are added thereto. For example, CsI is mixed with sodium iodide (NaI) at an appropriate ratio, as described in JP 54-035060 B. It is preferred that an activator material such as thallium (Tl), europium (Eu), indium (In), lithium (Li), potassium (K), rubidium (Rb) or sodium (Na) is included in CsI by the process of vapor deposition, as described in, for example, JP 2001-059899 A. In the invention an activator of sodium (Na), thallium (Tl) or europium (Eu) is preferred and thallium (Tl) is more preferred.

In the invention, it is preferred to use, as raw materials, cesium iodide and an additive containing at least one thallium compound. Namely, thallium-activated cesium iodide (CsI: Tl), which exhibits a broad emission wavelengths firm 400 to 750 nm, is preferable.

Such an additive containing at least one thallium compound may use various thallium compounds (that is, a compound having oxidation number of +I or +III).

In the invention, a preferable thallium compound is thallium bromide (TlBr), thallium chloride (TlCl) or thallium fluoride (TlF, $TlF_3$).

The melting point of a thallium compound related to the invention is preferably within the range of 400 to 700° C. A melting point higher than 700° C. results in uneven distribution of an additive within columnar crystals, leading to lowering of emission efficiency. In the invention, the melting point refers to a melting point under ordinary temperature and pressure.

The content of a thallium compound in the phosphor layer related to the invention, which is desirably optimized in accordance with its purpose or performance, is preferably from 0.001 to 50 mol % of the content of cesium iodide, and more preferably from 0.1 to 10.0 mol %.

An additive content of not less than 0.001 mol % of the cesium iodide content, which results in enhanced emission luminance, as compared to luminance obtained by cesium iodide alone, is preferable to achieve the intended omission luminance. A content of not more than 50 mol %, which enables to maintain characteristics or functions of cesium iodide, is preferable.

The thickness of a phosphor layer is preferably within a range of from 50 to 600 μm, and in cases when using a resin as a support, the thickness of a phosphor layer is preferably within a range of from 50 to 500 μm in consideration of damage during cutting. Further, the thickness is more preferably within a range of from 120 to 400 μm for use in medical care to balance luminance and sharpness.

In the invention, it is preferred that a phosphor layer is formed on a support by a process of vapor deposition of raw materials of a phosphor (scintillator) and then cut to a prescribed size.

Thereby, the image fanning area of a scintillator panel is broadened. The use of a resin as a support makes it feasible to decrease the thickness of the scintillator panel, which becomes suitable for a detector for use in a human mouth or a flat panel detector of a cassette size. It is also preferable to use a flexible resin support, whereby contact of a scintillator panel with the surface of a flat light-receiving element becomes uniform over the whole surface, resulting in uniform image characteristics within the surface area.

Further, cutting is conducted after completion of vapor deposition, so that it is not necessary to conduct vapor deposition onto the individual supports. Vapor deposition is conducted at a maximum size which can be prepared by the vapor deposition apparatus and cutting to a desired size can be performed, which is advantageous in terms of production efficiency and delivery date.

Void Fraction:

Columnar crystals of the foregoing phosphor layer extend vertically on the support and a void is formed between adjacent columnar crystals. Light is reflected on the interface between a columnar crystal and the void, resulting in an optical guiding effect, as described earlier.

The void fraction described earlier refers to the ratio of a void area to the sum of sectional areas of columnar crystals and the void area in the section in which a phosphor layer is cut parallel to the support.

The invention is characterized in that the difference that deducts the average void portion of the edge portion from the average void fraction of the base portion of a phosphor layer is not less than 5% and not more than 25%, and the void fraction decreases from the base portion to the edge portion.

Thus, the void fraction is sloped in the thickness direction of the phosphor layer, whereby enhancements of impact resistance and luminance can be achieved, while maintaining image sharpness.

A change in void fraction of the base portion of the phosphor layer preferably is not less than 10% and not more than 25%. This is because a change in void fraction of not more than 25% results in enhanced impact resistance and a change of the void fraction of not less than 10% achieves enhanced sharpness and luminance, in which the change in void fraction of the base portion is referred to below).

Herein, the base portion of a phosphor layer refers to the area within 30% in the thickness direction from the edge face of the support side of a phosphor layer and the edge portion of the phosphor layer refers to the area within from 60% to 100% in the thickness direction from the support side of the phosphor layer. Further, an area of from 30% to 60% in the thickness direction from the edge face of the support side of the phosphor layer refers to an intermediate portion.

The average void fraction of the base portion is an average value of void fractions at five portions which are determined from sections when cut into five portions at equivalent intervals from the edge of a phosphor layer of the support side to the position of 30% in the thickness direction.

Similarly, the average void fraction of the edge portion is an average value of void fractions at five portions which are determined from sections when the edge portion of a phosphor is cut into five portions at equivalent intervals in the thickness direction.

Change in void fraction of base portion=(void fraction at position of 5% of phosphor layer in thickness direction from edge of phosphor layer of support side)−(void fraction at position of 30% of phosphor layer in thickness direction from edge of phosphor layer of support side)

The change in void fraction of the base portion, as described above is preferably within a range of from 10% to 25% in terms of sharpness and luminance.

The average void fraction of the whole phosphor layer from the base portion to the edge portion is preferably within a range of from 10 to 25% in terms of impact resistance, sharpness and relative luminance.

The foregoing void fraction can be determined in such a manner that a phosphor layer of a scintillator panel is cut parallel to the support, and a scanning electronmicrograph of the section is scanned by using imaging software to perform binarization of the phosphor portion and the void portion.

In the phosphor layer related to the invention, activator concentration is varied with growth of columnar crystals, making it feasible to vary and control the void fraction in the thickness direction.

An activator at a high concentration results in an increase of the void fraction, and an activator at a high concentration leads to a decrease of the void fraction. Specific examples thereof include a technique in which a boat containing cesium iodide and a boat containing an activator and cesium iodide are placed in a vacuum vessel of a vapor deposition apparatus and the heating temperature of the latter boat is controlled in accordance with the stage of growth of columnar crystals to control the activator concentration.

The void fraction increases by lowering the substrate temperature at the time of deposition. It is preferred that the columnar diameter of a phosphor at the base portion of a phosphor layer is smaller than the columnar diameter of a phosphor at the edge portion and the phosphor is continuous from the base portion to the edge portion of the phosphor layer.

Reflection Layer:

In the invention, it is preferred to provide a reflection layer on a resin support, whereby emitted light from a phosphor layer is reflected, leading to enhanced light extraction efficiency. Such a reflection layer is formed preferably with a material containing at least an element selected from the group consisting of Al, Ag, Cr, Cu, Ni, Ti, Mg, Rh, Pt and Au. It is specifically preferred to use a thin film containing the foregoing element as a main component, for example, Ag film and Al film. Such a thin film may be in the form of two or more layers. The thickness of a reflection layer is preferably from 0.005 to 0.3 µm in terms of emission extraction efficiency, and more preferably from 0.01 to 0.2 µm.

Sublayer:

In the invention, it is preferred to provide a sublayer between a support and a phosphor layer, or between a reflection layer and a phosphor layer. Such a sublayer may be formed by forming a layer with poly(p-xylylene) through a chemical vapor deposition method (CVD method), or a method using a polymeric binding material (binder), but the method using a polymeric binding material (binder) is preferred in terms of adhesion. The thickness of a sublayer is preferably from 0.5 to 4 µm. Namely, a thickness of not more than 4 µm is preferable, which lessens light scattering within a sublayer, leading to enhanced sharpness. A thickness of not less than 0.5 µm is also preferred, which inhibits occurrence of disorder of columnar crystallinity caused by heat generation at the time of blade dicing. In the following, there will be described constituent elements of a sublayer.

Polymer Binder:

The foregoing sublayer is formed preferably by coating a polymeric hinder (hereinafter, also denoted as a binder) dissolved or dispersed in a solvent, followed by drying. Specific examples of a polymeric binder include polyurethane, vinyl chloride copolymer, poly[(vinyl chloride)-co-(vinyl acetate)], poly[(vinyl chloride)-co-(vinylidene chloride)], poly[(vinyl chloride)-co-acrylonitrile], poly(butadiene-co-acrylonitrile), polyimide resin, poly(vinyl butyral), polyester, cellulose derivatives (e.g., nitrocellulose), Poly(styrene-co-butadiene), various synthetic rubber resins, a phenol resin, epoxy resin, urea resin, melamine resin, phenoxy resin, silicone resin, acryl resin, and urea formaldehyde resin. Of these, an acryl resin, polyurethane resin, polyester resin, vinyl chloride copolymer, poly(vinyl butyral) and nitrocellulose are preferably used.

The foregoing polymeric binder preferably is polyurethane, polyester, vinyl chloride copolymer, poly(vinyl butyral) or nitrocellulose in terms of adhesiveness to the phosphor layer. A polymer exhibiting a glass transition temperature (Tg) of 30 to 100° C. is also preferred in terms of adhesion between deposited crystals and a support. In view thereof, an acryl resin, or polyester resin is preferred.

Specific examples of a solvent used for preparation of a sublayer include a lower alcohol such as methanol, ethanol, n-propanol or n-butanol; a chlorine-containing hydrocarbon such as methylene chloride or ethylene chloride; a ketone such as acetone, methyl ethyl ketone, or methyl isobutyl ketone; an aromatic or alicyclic compound such as toluene, benzene, xylene, cyclohexane or cyclohexanone; an ester of a lower fatty acid and a lower alcohol such as methyl acetate, ethyl acetate, or butyl acetate; dioxane and an ether such as ethylene glycol monomethyl ether or ethylene glycol monoethyl ether.

The sublayer related to the invention may contain a pigment or dye to inhibit scattering of light emitted from a phosphor (scintillator) or to achieve an enhancement of sharpness or the like.

Protective Layer:

A protective layer primarily aims to prevent a phosphor crystal from cracking at the time of blade dicing, to maintain moisture-proofing over a period of time until being set into a detector enclosure and also to inhibit corrosion of the flat light receiving element side, caused by contact of a scintillator panel with a flat light receiving element. Based on the premise that a scintillator panel is maintained in a low-moisture environment over a period until the scintillator panel and a flat light-receiving element are coupled, a protective layer may exist on a contact portion with the flat light-receiving element and it is not necessary to cover the cut face side of a phosphor layer, provided that an enclosure of a flat panel detector preferably is lower in moisture permeability than the protective layer.

The foregoing protective layer can be formed by using various kinds of materials. For instance, a poly(p-xylylene) layer is formed by a CVD method. Specifically, a poly(p-xylylene) layer is formed on the surfaces of a phosphor (scintillator) and a support to form a protective layer.

The thickness of a poly(p-xylylene) layer is preferably not less than 2 µm and not more than 10 µm, and the thickness of an adhesive layer is preferably not less than 10 µm and not more than 18 µm when adhered to a light receiving element. Namely, the thickness of an adhesive layer is preferably not less than 10 µm to secure adhesion force but a total thickness of a poly-p-xylylene layer and an adhesive layer is preferably not more than 20 µm, in which diffusion of light emitted from a scintillator is increased in the space between a light receiving element and a scintillator panel, preventing a flat panel detector from a lowering of sharpness.

In another embodiment, a hot-melt resin, as a protective layer may be used on a phosphor layer. Such a hot-melt resin can also allow a scintillator panel to adhere onto the surface of a planar light receiving element. A hot-melt resin which is mainly composed of a polyolefin, polyester or polyamide resin is suitable but is not limited to those. The thickness of a hot-melt resin is preferably not more than 20 µm.

It was found that, when using a rigid support such as carbon, aluminum or glass, formation of a protective layer of poly(p-xylylene) or a hot-melt resin on the phosphor layer surface made it feasible to perform blade dicing to a prescribed size without accompanying cracking of crystals. In the invention, such blade dicing refers to cutting by using a blade which is generally used in dicing of silicon wafers. In cases when a support is glass, laser dicing is also feasible.

The upper portion and the lateral side of a scintillator layer (corresponding to the phosphor layer of the invention) and the periphery of a support are covered with poly(p-xylylene), and thereby, enhanced moisture resistance is achieved. A hot-melt resin can achieve not only moisture resistance but also adhesion between a scintillator panel and a flat light-receiving element.

It is also desirable in terms of impact absorption to form a layer of a resin such as poly(p-xylylene) or a hot-melt resin which is capable of penetrating between phosphor columnar crystals to some extent.

In another embodiment of a protective layer, a polymeric protective film may be provided on a phosphor layer.

Taking into account void formation, protectiveness of a scintillator (phosphor) layer, sharpness, moisture resistance and workability, the thickness of the foregoing polymeric protective film is preferably not less than 12 μm and not more than 60 μm, and more preferably not less than 20 μm and not more than 40 μm. Further, taking into account sharpness, radiographic image unevenness, production stability and workability, a haze factor preferably is not less than 3% and not more than 40%, and more preferably not less than 3% and not more than 10%. The haze factor is a value which is determined by NDH 5000W, produced by Nippon Denshoku Kogyo Co., Ltd. A desired haze factor can also be achieved by using a polymer film which is selected from commercially available polymer films.

Taking into account photoelectric conversion efficiency and emission wavelength of a scintillator, the light transmittance of a protective film is preferably not less than 70% at 550 nm but substantially, a transmittance of 99 to 70% is preferred since a film with a light transmittance of 99% or more is not industrially available.

Taking into account protectiveness and deliquescence of a phosphor layer, the moisture permeability of a protective film (which is measured based on JIS Z 0208) is preferably not more than 50 g/m$^2$·day (40° C., 90% RH) and more preferably not more than 10 g/m$^2$·day (40° C. 90% RH). Since a film having a moisture permeability of not more than 0.01 g/m$^2$·day (40° C. 90% RH) is not industrially available, the moisture permeability preferably is substantially not less than 0.01 g/m$^2$·day (40° C. 90% RH) and not more than 50 g/m$^2$·day (40° C. 90% RH), and more preferably not less than 0.1 g/m$^2$·day (40° C. 90% RH) and not more than 10 g/m$^2$·day (40° C. 90% RH).

Taking into account protection and deliquescence of a phosphor layer, the moisture permeability of a housing constituting a flat panel detector (which is measured based on JIS Z 0208) is preferably not more than 50 g/m$^2$·day (40° C. 90% RH) in terms of total surface area average, and more preferably not more than 10 g/m$^2$·day (40° C. 90% RH).

Support:

A support of the scintillator panel of the present invention may employ various materials, such as (1) carbon fiber reinforced plastics (CFRP), (2) carbon board (obtained by solidifying charcoal or paper through carbonization), (3) carbon support (graphite support), (4) plastic support, (5) glass support, (6) various metal supports, and (7) one in which a support as described in (1) to (6) is thinly formed and sandwiched with an expanded plastic. When producing a scintillator panel by a conventional vapor deposition process, a support requires heat resistance, so that a phosphor layer is generally deposited on a rigid support, such as aluminum or amorphous carbon. The thickness of such a rigid support is preferably not less than 0.3 mm and not more than 1.0 mm.

A support usable in the invention preferably employs a resin film which can be easily cut after deposition of a phosphor layer and is also bendable at the time when coupling a scintillator panel to a flat light receiving element. There are usable resin films (plastic films) such as cellulose acetate film, polyester film, polyethylene terephthalate (PET) film, polyethylene naphthalate (PEN), polyamide film, polyimide film, triacetate film, polycarbonate film and a carbon fiber reinforced resin sheet. A polymer film containing a polyimide or polyethylene naphthalate is specifically preferable when forming phosphor columnar crystals with a raw material of cesium iodide by a process of vapor phase deposition.

Such a resin film preferably is 50 to 200 μm thick and is also preferably flexible.

Herein, the flexible support refers to a support exhibiting an elastic modulus at 120° C. (also denoted as E120) of 1000 to 6000 N/mm$^2$. Such a support preferably is a polymer film containing a polyimide or polyethylene naphthalate.

In the region showing a linear relationship between strain and corresponding stress which is measured by using a tensile strength tester based on JIS C 2318, the elastic modulus is calculated as the slope of the straight portion of the stress-strain curve, that is, stain divided by stress, which is also referred to as a Young's modulus. In the invention, such a Young's modulus is defined as the elastic modulus.

The support used in the invention preferably exhibits an elastic modulus at 120° C. (E120) of 1000 to 6000 N/mm$^2$, and more preferably 1200 to 5000 N/mm$^2$.

Specific examples thereof include a polymer film comprising polyethylene naphthalate (E120=4100 N/mm$^2$), polyethylene terephthalate (E120=1500 N/mm$^2$), polybutylene naphthalate (E120=1600 N/mm$^2$), polycarbonate (E120=1700 N/mm$^2$), syndiotactic polystyrene (E120=2200 N/mm$^2$), polyether imide (E120=1900 N/mm$^2$), polyimide (E120=1200 N/mm$^2$), polyarylate (E120=1700 N/mm$^2$), polysulfone (E120=1800 N/mm$^2$) or polyether sulfone (E120=1700 N/mm$^2$).

These may be used singly or mixedly, or laminated. Of these polymer films, a polymer film comprising polyimide or polyethylene naphthalate is preferred.

Adhesion of the scintillator panel to the surface of a planar light receiving element is often affected by deformation of a support or its warpage during deposition, rendering it difficult to achieve a uniform image quality characteristic within the light receiving surface of a light receiving element. In such a case, a 50-200 μm thick polymer film is used as the support (substrate), whereby the scintillator panel is deformed with being fitted to the form of the surface of a planar light receiving element, rendering it feasible to achieve uniform sharpness over all of the light-receiving surface of the flat panel detector.

Preparation Method of Flat Panel Detector:

There will be described a typical flat panel detector related to the invention with reference to the drawing.

Figure 1A:
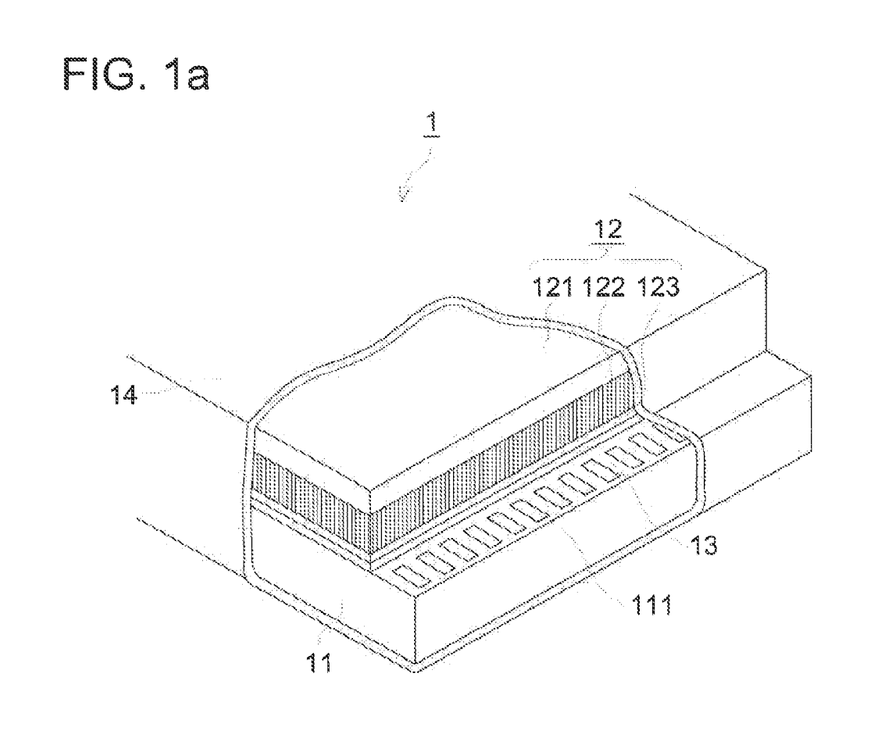
FIG. 1a shows a schematic sectional view illustrating an example of constitution of a flat panel detector.

FIG. 1a is a perspective view showing schematic constitution of a flat panel detector 1. A scintillator panel 12 is adhered to a light receiving element 11 through an adhesion layer 13. A support 121 and a phosphor layer 122 have the same size. There are coupled the entire surface of a light receiving picture element section other than a signal extraction section 111 and a portion of a phosphor layer 122. The entire flat panel detector is sealed with an enclosure 14.

Figure 1B:
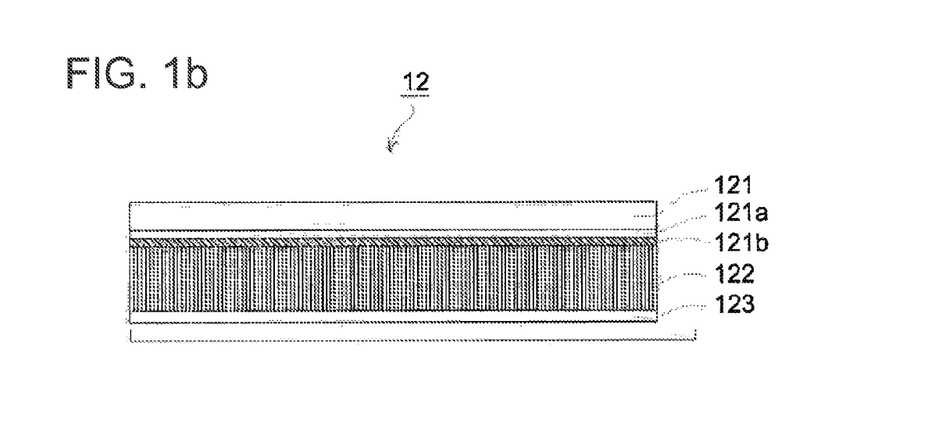
FIG. 1b shows a schematic sectional view of a scintillator panel.

FIG. 1b is a sectional view of a scintillator panel, in which the support 121, a reflection layer 121a, a sublayer 121b, the phosphor layer 122 and the protective layer 123 are provided in this order. The protective layer 123 does not exist on the section of the phosphor layer 122.

Cutting Method of Scintillator Panel:

There will be described a typical example of a cutting method of a scintillator panel related to the invention, with reference to figures.

Figures 2A, 2B:
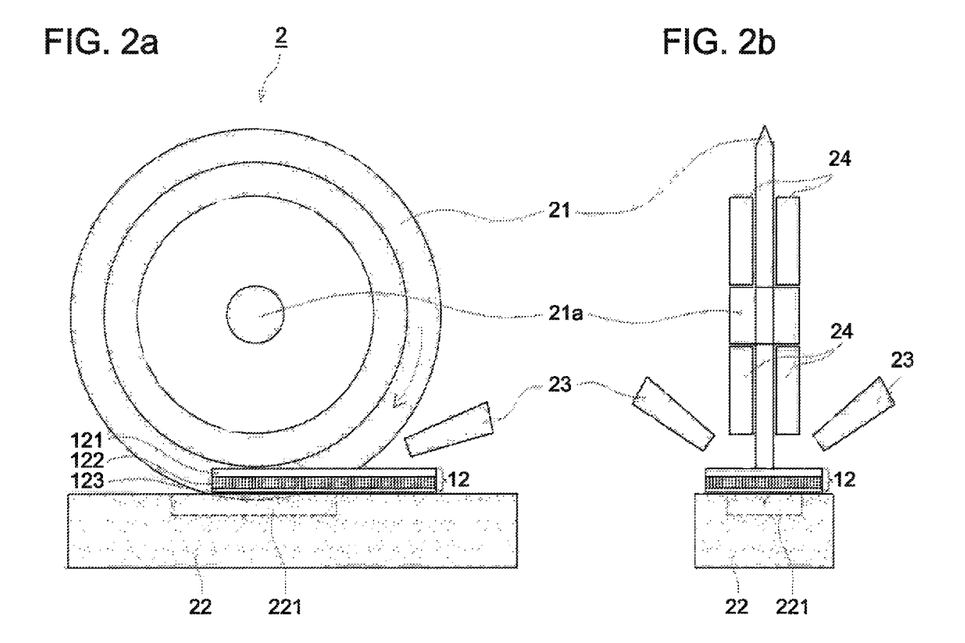
FIGS. 2a and 2b show schematic sectional views of a cutting device used in a cutting process.

FIGS. 2a and 2b show an example of blade dicing of a scintillator panel 12 after formation of the protective layer 123. The scintillator panel 12 was mounted on a dicing board 22 of a dicing apparatus 2, while the protective layer (123) side being downward. The scintillator panel 12 is cut by a blade 21 from the support (121) side. The support 121 is a 1 mm thick amorphous carbon.

The blade 21 cuts the scintillator panel 12, while rotating around a rotating shaft 21a. The dicing board 22 is provided with a groove 221. Further, supporting members 24 are provided on both sides of the blade. Cooling air is blown onto the cutting section through a nozzle 23 from both sides of the blade 21 to cool friction heat. The temperature of such cooling air is not more than 4° C. and the room humidity is maintained at 20% or less to inhibit dewing.

A glass support can also be cut by a laser dicing apparatus. A resin support is cut preferably by using a laser cutting apparatus, as shown in FIG. 3a.

Figure 3A:
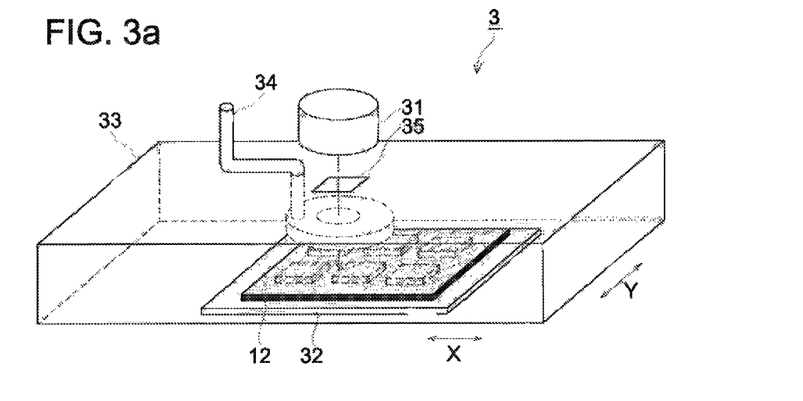
FIG. 3a shows a schematic perspective view of another example of a cutting device used in the cutting process.

FIG. 3a shows an example of laser cutting of a scintillator panel 12 which is not provided with a protective layer.

A laser cutting apparatus 3 is provided with a purging room 33 formed in a box shape. The purging room 33 has an internally closed space so that dust or the like suspended in the external space does not enter the internal space. The interior of the purging room 33 preferably is preferably under an atmosphere of low humidity. There is provided a translucent window 35 to transmit a laser light on the upper surface of the purging room 33. There is also provided a discharging tube 34 to introduce suspended materials such as dust to the outside of the purge room 33.

The scintillator panel 12 is placed on a support board 32 of the laser cutting apparatus 3, while the support (121) side being downward and is adsorptively retained on the support board 32. Accordingly, the scintillator panel 12 is retained in a phosphor layer (122)-upward fashion.

The scintillator panel 12 which is placed on the support board 32 is positioned immediately below a laser exposure section of a laser generator 31 by a support board transfer means (not shown in the drawing). The scintillator panel 12 is exposed to a laser light ejected from the laser generator 31.

Exposure is conducted under the condition of YAG-UV (yttrium/aluminum/garnet crystal, 266 nm wavelength) at a pulse laser of 5000 Hz frequency and 20 μm beam diameter and an output of 300 mW. Cutting is conducted, while moving the scintillator panel 12 by the support board transfer means (which is not shown in the drawing).

Figure 3B:
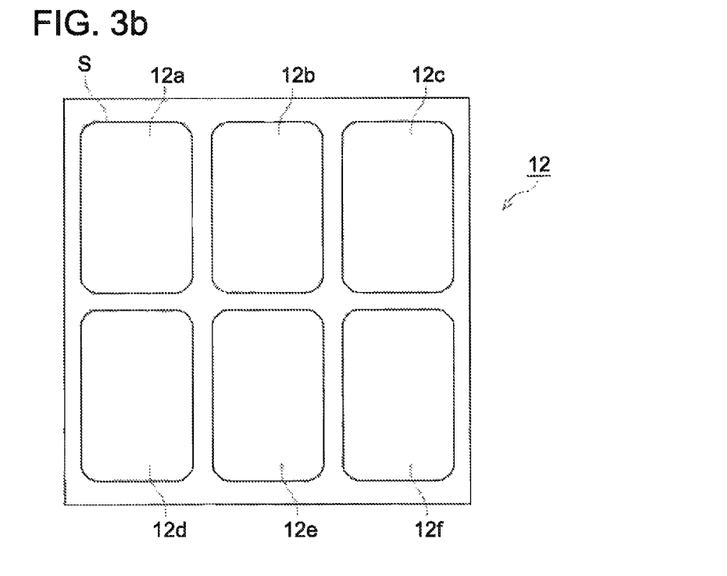
FIG. 3b shows a plan view representing plural scintillator panels cut out by cutting.

FIG. 3b shows an example of plural scintillator panels cut by lasers. "S" is a laser-cut portion. Namely, scintillator panels 12a, 12b, 12c, 12d, 12e and 12f are cut from the scintillator panel 12.

Vapor Deposition Method of Scintillator Panel:

There will be described a typical example of a vapor deposition method of a scintillator panel related to the invention with reference to the drawings.

Figure 4:
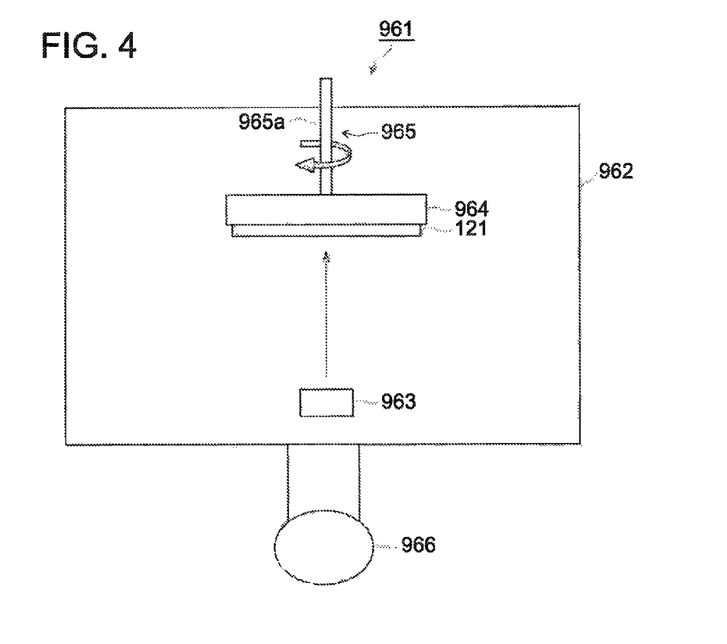
FIG. 4 shows a schematic sectional view of an example of a device used for formation of a phosphor layer.

Vapor Deposition Apparatus:

As shown in FIG. 4, a vapor deposition apparatus 961 is provided with a box type evacuation vessel 962 and a boat 963 for use in vacuum deposition is disposed within the vacuum vessel 962. The boat 963 is a member filled with an evaporation source and electrodes are connected to the boat 963 so that, when an electric current is applied through the electrodes, the boat generates heat through the Joule heat phenomenon. In production of the scintillator panel 12, the boat 963 is filled with a mixture including cesium iodide and an activator compound and application of an electric current to the boat 963 causes the mixture to be heated and vaporized.

An aluminum crucible wound with a heater may be used as a filling member or a refractory metal heater may be applied.

A holder 964 to hold the support 121 is disposed within the evacuation vessel 962 and above the boat 963. The holder 964 is provided with a heater (not shown in the drawing) and operating the heater can heat the support 121 held by the holder. Heating the support 121 makes it feasible to separate or remove material adhered to the surface of the support 121, to inhibit formation of impurities between the support 121 and the phosphor layer, to strengthen adhesion of the support 121 onto the phosphor layer 122 or to control surface quality of the phosphor layer 2 formed on the support 121.

A rotation mechanism 965 to rotate the holder 964 is arranged to the holder. The rotation mechanism is constituted of a rotation shaft 965a connected to the holder 964 and a motor (not shown in the drawing) as a driving source. Driving the motor rotates the rotation shaft 965a and thereby, the holder 964 can be rotated, while being opposed to the boat 963.

The vapor deposition apparatus 961 is provided with a vacuum pump 966 used for the vacuum vessel 962 in addition to the foregoing constitution. The vacuum pump 966 evacuates the interior of the vacuum vessel 962 to allow gas to be introduced into the interior of the vacuum vessel 962. Operating the vacuum pump 966 can maintain the interior of the vacuum vessel with gaseous atmosphere at a prescribed pressure.

Figure 5:
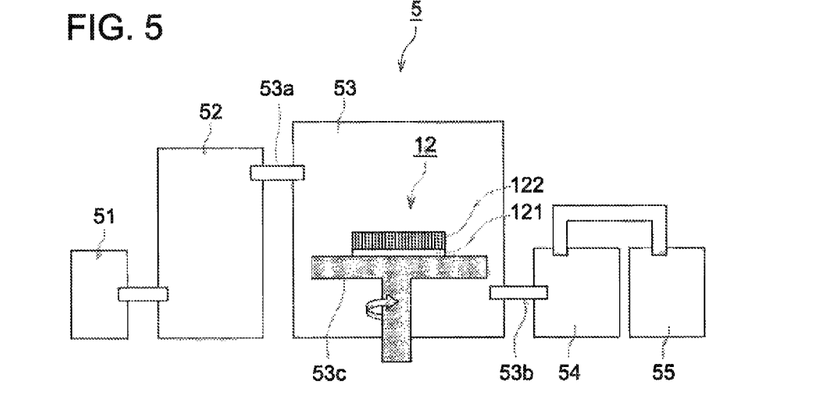
FIG. 5 shows a schematic sectional view of an example of an apparatus used for formation of a protective layer.

CVD Apparatus:

FIG. 5 shows an example of formation of a protective layer composed of poly(p-xylylene) on the surface of the phosphor layer 122 of the scintillator panel 12.

A CVD apparatus 5 is constituted of an evaporation room 51 in which di-p-xylylene as a raw material for poly(p-xylylene) is inserted and evaporated, a pyrolysis room 52 in which evaporated di-p-xylylene is heated and pylolyzed to form radicalized di-p-xylylene, a vapor deposition room 53 in which such radicalized di-p-xylylene is allowed to be deposited on a scintillator formed on the surface of the phosphor layer 122 on the support 121, a cooling room 54 to perform deodorization and cooling, and an evacuation system 55 provided with a vacuum pump. As shown in FIG. 5, the vapor deposition room 53 is provided with a turn table 53c (deposition board) to perform deposition of poly(p-xylylene) together with an inlet 53a to introduce radicalized poly(p-xylylene) and an outlet 53b to exhaust excess poly(p-xylylene).

The scintillator panel 12 is placed with the phosphor layer 122 upward on the turn table 53c of the vapor deposition room 53. Then, heating to 175° C. is conducted in the evaporation room 51 to perform evaporation; heating to 690° C. is conducted in the pyrolysis room 52 to form di-p-xylylene radicals, which are introduced to the vapor deposition room 53 through the inlet 53a and deposited onto the phosphor layer 122 to form a 3 μm thick protective layer 123 [poly(p-xylylene) film], while the interior of the vapor deposition room 53 is maintained at a vacuum of 13 Pa. The turn table 53c is rotated at a rate of 4 rpm. Further, excess poly(p-xylylene) is exhausted from the outlet 53b and introduced to a cooling room 54 to perforin cooling, a cooling room 54 to perform deodorization and cooling, and to an evacuation system 55 provided with a vacuum pump.

Scintillator Panel:

Next, there will be described a preparation method of a scintillator panel 12 related to the invention.

The vapor deposition apparatus 961 shown in FIG. 3 can be appropriately used in a preparation method of the radiation scintillator panel 12. There will be described a preparation method of the radiation scintillator panel 12 by using the vapor deposition apparatus 961.

Formation of Reflection Layer:

A metal thin film as a reflection layer (Al film, Ag Film or the like) is formed on one of the surfaces of a support 121 by a sputtering method. In cases when using a resin film as a support, various kinds of film in which Al film is deposited on resin an through sputtering, is commercially available and usable as a support 121 of the invention.

Formation of Sublayer:

The sublayer 123 is formed by coating the composition of a polymeric binder dispersed or dissolved in an organic solvent, followed by being dried. A hydrophobic resin such as an acryl resin, polyester resin or polyurethane resin is preferably used for such a polymeric binder in terms of adhesiveness and corrosion resistance for the reflection layer.

Formation of Phosphor Layer:

The support 121 provided with a reflection layer and a sublayer is mounted on the holder 964, and one of plural boats 963 (which are not shown in the drawing) is filled with cesium iodide and another boat is filled with a powdery mixture of cesium iodide and thallium iodide as an activator (preliminary step). The spacing between the boat 963 and the support 121 is set to a distance of 100 to 1500 mm and vapor deposition is conducted, while maintaining the spacing as set. Preferably, the spacing between the boat 963 and the support 121 is kept not less than 400 mm and not more than 1500 mm and vapor deposition is conducted, while simultaneously heating plural boats (963).

In the phosphor layer related to the invention, the relative content of an activator is preferably from 0.1 to 5 mol %, and the void fraction can be controlled by variation of an activator concentration in the growth direction of columnar crystals.

After completing treatments in the foregoing preliminary step, the evacuation pump 966 is operated to evacuate the interior of the vacuum vessel 962 to a vacuum atmosphere of not more than 0.1 Pa (vacuum atmosphere-forming step). The vacuum atmosphere refers to an atmosphere at a pressure of not more than 100 Pa and an atmosphere at a pressure of not more than 0.1 Pa is suitable.

Next, inert gas such as argon or the like is introduced into the vacuum vessel 962 and the interior of the vacuum vessel 962 is maintained at a vacuum atmosphere of from 0.001 to 5 Pa, preferably from 0.01 to 2 Pa. Thereafter, a heater of the holder 964 and a motor of the rotation mechanism 965 are driven, whereby the support 121 fixed to the holder is rotated with heating, while being opposed to the boat 963. The temperature of the support 121 on which a phosphor layer is formed is controlled preferably to 25 to 50° C. at the time of initiating evaporation and is maintained preferably at a temperature of 100 to 300° C., and more preferably 150 to 250° C. during evaporation.

While maintaining such a state, an electric current is applied from an electrode to the boat 963 to heat a mixture containing cesium iodide and thallium iodide to a temperature of approximately 700° C. over a prescribed period of time to evaporate the mixture. Consequently, a number of columnar crystals in each of which a void fraction is different between base portion and edge portion grow successively on the surface of the support 121 to obtain crystals with an intended thickness (vapor deposition step). Thereafter, a support on which cesium iodide is deposited is taken out and the phosphor surface is cleaned by an adhesive roller.

The foregoing steps may be modified or degraded within the range without departing from the scope of the present invention.

As one of such modifications or design alterations, resistance heating in the foregoing vapor deposition stage may be replaced by an electron beam treatment or a high-frequency induction treatment. In the embodiments of the present invention, a heating treatment by a resistance heating method is preferred in terms of being easily treated by a relatively simple constitution at relatively low-cost and being applicable to various substances. Application of a resistance heating method to a heating treatment makes it feasible to achieve both a heating treatment of a mixture of cesium iodide and thallium iodide, and a vapor deposition treatment.

As another modification or design alteration, a shutter (not shown in the drawing) to cut off the space from the boat 963 to the holder 964 may be disposed between the boat 963 and the holder 964 of the vapor deposition apparatus 961. In such a case, it can be prevented such that a substance other than the objective material is evaporated at the initial stage of evaporation and adheres to the support 121, thereby preventing columnar crystals from abnormal growth caused by foreign material generated at the initial stage of evaporation.

Formation of Protective Layer:

In the CVD apparatus shown in FIG. 5 is provided the protective layer 123 composed of poly(p-xylylene). Alternatively, a hot-melt resin is coated on a peeling sheet coated with a peeling agent; then, the hot-melt resin face is disposed onto the phosphor layer surface of a scintillator panel and pasted together with compressing with a roller heated at 120° C. to form the protective layer 123. In cases when using an adhesive for adhesion onto the surface of a light receiving element, the thickness of the protective layer is controlled so that the total thickness of the protective layer and then adhesive layer is not more than 20 µm. In cases when using a resin film as a support, formation of a protective layer may be conducted after cutting a scintillator panel, as described later.

Coupling:

The surface of the phosphor layer side of the foregoing scintillator panel is jointed with the light-receiving surface of the foregoing light receiving element to be integrated, which refers to coupling. Methods for performing such coupling include, for example, a technique of pressure-bonding both surfaces by using an auxiliary material such as a cushioning material, a technique of adhesion with an adhesive and a technique of sticking together with matching oil.

Adhesion of Scintillator Panel to Planar Light Receiving Element:

The scintillator panel 12 and the planar light receiving element 11 are pasted together with an adhesive layer 13. In adhesion, pressure of 10 to 500 g/cm$^2$ is applied thereto until the adhesive is solidified. Application of pressure removes bubbles from the adhesive layer. When using a hot-melt resin for the protective layer 123, the hot-melt resin is heated at a temperature higher by 10° C. than the melt initiation temperature of the hot-melt resin, while compressing at a pressure of 10 to 500 g/cm$^2$ and after allowed to stand over 1 to 2 hours, cooling is gradually conducted. Rapid cooling damages pixels of a light receiving element by shrink stress. Preferably, cooling is conducted to a temperature of 50° C. or lower at a rate of not more than 20° C./hour.

An adhesive used in the adhesive layer 13 can use, for example, a cold curing type adhesive of acryl, epoxy or silicone. There is also usable a rubber type adhesive, as an elastic adhesive resin.

Examples of rubber type adhesive resins include a block copolymer such as styrene-isoprene-styrene, and a synthetic rubber such as polybutadiene or polybutylene. Preferred examples of commercially available rubber type adhesive include a one component type RTV rubber KE 420 (produced by Shinetsu Kagaku Kogyo Co. Ltd.).

A silicone adhesive may employ a peroxide curing type or addition condensation type, singly or in combination. Further, such a silicone adhesive may be mixed with an acryl type adhesive or a rubber type adhesive. There may be used an adhesive in which a silicone component is allowed to pond to a polymeric main chain or side chain of an acryl type adhesive.

In cases when using an acryl resin as an adhesive, it is preferable to use a resin obtained by allowing a radical-polymerizable monomer containing an acrylic acid ester having an alkyl side chain of one to fourteen carbon atoms. It is also preferable to add, as a monomer component, an acrylic acid ester having a polar side chain such as a hydroxyl group, a carboxyl group or an amino group, or other vinyl monomers.

A viscous optical grease is also usable in the scintillator panel 12 or the light receiving element 11. There is usable any commonly known one which is highly transparent and viscous. Preferred examples of a commercially available optical grease include silicone oil KF 96H (Million CS, produced by Shinetsu Kagaku Kogyo Co. Ltd.).

EXAMPLES

In the following, the present invention will be described with reference to examples, but the invention is by no means limited to these.

Preparation of Support:

A silver reflection layer (0.10 μm thick) was formed on each of supports A-1 to P-3 with a size of 600 mm×600 mm in height and width by a sputtering method.

The material and thickness of each of the supports were as follows:

| A-1 | Aluminum | 0.2 mm |
| A-2 | Aluminum | 0.5 mm |
| C-1 | Amorphous carbon | 0.5 mm |
| C-2 | Amorphous carbon | 1.0 mm |
| C-3 | Amorphous carbon | 1.5 mm |
| P-1 | Polyimide film | 0.030 mm |
| P-2 | Polyimide film | 0.125 mm |
| P-3 | Polyimide film | 0.225 mm |

Preparation of Sublayer:

| Vylon 20SS (Polyester resin, produced by Toyobo Co., Ltd.) | 300 parts by mass |
| Methyl ethyl ketone (MEK) | 200 parts by mass |
| Toluene | 300 parts by mass |
| Cyclohexanone | 150 parts by mass |

The foregoing composition was mixed and dispersed by a ball mill over 15 hours to obtain a coating solution used for subbing. The thus obtained coating solution was coated on the reflection layer side of the foregoing support by a spin coater so that the dry thickness was 1.0 μm, and then dried at 100° C. over 8 hours.

Formation of Phosphor Layer:

Phosphor 1 (CsI alone) was placed into a boat 1 and phosphor 2 (CsI containing Tl in an amount of 0.03 mol % of CsI) was placed into a boat 2.

In an evaporation apparatus, the foregoing support provided with a sublayer was placed onto a support holder installed with a support rotation mechanism. The boats 1 and 2 in which the foregoing phosphors were placed were disposed in the vicinity of the bottom of a vacuum vessel and on the circumference of a circle centered on the vertical center line to the support. The distance between the support and the evaporation source was adjusted to 500 mm and the distance between the center line vertical to the support and the evaporation source was adjusted to 300 mm. Further, a shutter (not shown in the drawing) was disposed between each of the boats and a holder to prevent substances other than the objective material from adhering onto the phosphor layer.

Subsequently, after the interior of the vacuum vessel was evacuated, the degree of vacuum was controlled to 0.5 Pa, while introducing Ar gas and the temperature of the support was maintained at 30° C., while rotating the support at a rate of 10 rpm. Subsequently, the temperature in the interior of the boat 1 was raised to the prescribed temperature by resistance heating. Subsequently, evaporation of the phosphor 1 was initiated and then, the temperature of the support (substrate) was raised to 200° C. and the phosphor 2 was evaporated. Evaporation was terminated when the thickness of the phosphor layer reached 200 μm. The Tl concentration of a columnar crystal was varied in the thickness direction of the phosphor, while controlling the temperature and period of time at the time of evaporation of the phosphor 1 and the phosphor 2 to obtain a phosphor layer in which the average void fraction of the whole phosphor layer was 20% and the change in void fraction was as shown in Table 1.

In a sample employing a support A-1 (0.2 mm thick aluminum) or a support P-1 (0.03 mm thick polyimide), deformation as sagging was caused by vapor deposition, making it difficult to continue subsequent work.

Accordingly, these supports were each adhered to a 1 mm thick aluminum auxiliary substrate and then, evaporation was conducted.

In these samples, the phosphor layer was easily damaged when peeling the auxiliary substrate. To solve such a problem, the phosphor layer was adhered to a planar light receiving element and then, the auxiliary substrate was peeled off. The thus obtained samples were evaluated as Examples 15 and 16. Examples 15 and 16, which had no problem in performance, needed to allow the support to adhere to such an auxiliary substrate and required more man-hours.

As can be seen from the foregoing, problems caused during vapor deposition were dissolved by use of an auxiliary substrate or by a process change. It was also proved that the thickness of a support mainly composed of a rigid material such carbon, aluminum or glass was preferably not less than 0.3 mm, and that of a support mainly composed of a resin film was preferably not less than 0.05 mm.

Formation of Protective Layer:

A protective layer composed of poly(p-xylylene) was formed as follows. The thus obtained scintillator panel was set into a CVD apparatus to form a protective layer comprising poly(p-xylylene). The thickness of such a poly(p-xylylene) layer was controlled to 3 μm. Specifically, in P-1, P-2 and P-3 which were each provided on a resin film support, a 3 μm thick protective layer was formed in a CVD apparatus after being cut to a prescribed size at the stage of cutting a scintillator panel.

An example of providing a protective layer of the foregoing poly(p-xylylene) film was denoted as "Pa" in the column of a protective layer in Table 1.

A protective layer formed of polymer protective film was obtained as follows. The obtained scintillator layer of a scintillator panel was covered with Barrier-Locks (with a coating) 1011 HG-CW (#12), produced by Toray Advanced Film Co., Ltd. to provide a protective layer formed of a polymeric protective film.

An example of providing the foregoing protective layer formed of a polymeric protective film was denoted as "BR" in the column of a protective layer in Table 1.

Coupling with Planar Light Receiving Element:

Scintillator panels in which the protective layer formed of a polymeric protective film, as described above was provided, were prepared by using a planar light receiving element of an effective image area provided with CMOS on the light receiving surface (Rad Eye 1 with a picture element size of 48 μm, produced by Rad-icon Imaging Corp.).

In Example 11 and Comparison 3, coupling was conducted with compression by a sponge. In Examples 1 to 10 and 12 to 16, and Comparisons 1, 2 and 4 to 7, coupling was conducted with an adhesive.

Coupling with Sponge:

In Example 11 and Comparison 3, coupling was conducted in such a manner that a scintillator panel and a planar light receiving element were jointed so that the phosphor layer side of a scintillator panel was opposed to the light receiving surface of a planar light receiving element, and loaded in a housing so that the support of the scintillator panel faced the cover of the housing, then, a sponge to control pressure was placed on the support the scintillator panel, the cover of the housing was fixed with screw threads, and a pressure of 30 g/cm$^2$ was applied thereto to perform coupling.

Coupling with Adhesive:

An acrylic adhesive of the composition described below was used for adhesion of the phosphor layer side of a scintillator panel to the light receiving surface of a planar light receiving element, except in Example 11 and Comparison 3.

It is known that, when coupled to a planar light receiving element, coupling is conducted by compression with some extent of curvature, and thereby, involved bubbles or the like are easily ejected, which is advantageous for the process. Accordingly, a scintillator panel in which a bendable resin support was used, was adhered to a planar light receiving element, while being bent at a curvature of a radius of 5 cm. A scintillator panel using an unbendable support, such as aluminum, amorphous carbon or glass, was adhered without being bent.

An adhesive of the present composition is easily releasable, making it easy to change the position before being thermally bonded.

Acrylic Adhesive:

To 100 parts by mass of a mixture (A), expressed in solid content, was added 1 part by mass of an aromatic isocyanate compound (B) described below. Further thereto was added 60 ppm in solid equivalent of dioctyl tin dilaurate and diluted with ethyl acetate to obtain an adhesive composition of 30% solids.

| (A) | |
| --- | --- |
| 2-Ethylhexyl acrylate | 50 parts by mass |
| Butyl acrylate | 30 parts by mass |
| Styrene | 19 parts by mass |
| 2-Hydroxyethyl methaorylate | 3 parts by mass |
| (B) | |
| Tolylene diisocyanate/trimethylolpropane adduct (trade name: Coronate L, produced by Nippon Polyurethane Co., Ltd.) | |

The foregoing adhesive was coated on the side of a protective layer (123) of a scintillator panel (12) so that the thickness was 10 μm and dried. Then, the scintillator panel and a CMOS portion were completely matched, while observing them by a stereo microscope. Thereafter, heating was conducted over 90 minutes in an atmosphere at 70° C. with pressing with a pressure of 100 g/cm$^2$, followed by gradual cooling, whereby the scintillator panel (12) was coupled to a planar light receiving element (11).

Then, a signal takeoff cable was connected to the connector portion of a planar light receiving element (Rad Eye 1), which was again set into a CVD apparatus, as shown in FIG. 5 to cover the overall surface of the scintillator panel and the planar light receiving element with a 50 μm thick poly(p-xylylene) film, and thereby, a flat panel detector provided with a non-moisture-permeable housing was obtained.

Evaluation of Scintillator Panel:

The thus obtained scintillator panels were evaluated with respect to void fraction, bending resistance, shock resistance, sharpness and DQE in accordance with the procedure described below.

Determination of Void Fraction:

A phosphor layer of each of the obtained scintillator panels was cut parallel to the support and a scanning electron micrograph of the cross-section was binarized to a phosphor portion and a void portion by using image processing software to determine void fractions of the base portion, an intermediate portion and an edge portion, and a change in void fraction of the base portion.

Evaluation of Flat Panel Detector:

Evaluation of Shock Resistance:

After a 500 g iron ball was allowed to fall onto a flat panel detector from a height of 20 cm, the flat panel detector was visually observed and evaluated. Thereafter, after being exposed to X-rays at a tube voltage of 40 kVp from the rear face side of the support, an obtained image on a flat panel detector was printed out by an output device and the obtained print image was visually evaluated with respect to shock resistance, based on the following criteria. Evaluation results are shown in Table 1.

5: No cracking was observed and a uniform image was obtained,

4: No cracking was observed and image quality was at a level of being barely noticed, 3: Cracking was observed and slight image defects were confirmed, which were still at a level of being acceptable in practice, 2: Cracking was observed and an apparent image defect was confirmed, which were at a level to cause problems in practice.

1: A large number of cracks were observed and many image defects were noted, which were at a level to cause problems in practice.

Evaluation of Bending Resistance:

With respect to examples of a resin support among the obtained scintillator panels, a flat panel detector which was prepared by being adhered onto a planar light receiving element at a curvature of a radius of 5 cm, was exposed to X-rays at a tube voltage of 40 kVp from the rear face side of the support, an obtained image on the flat panel detector was printed out by an output device and the obtained print image was visually evaluated with respect to bending resistance, based on the following criteria. The valuation results are shown in Table 1.

5: No cracking was observed and a uniform image was obtained,

4: No cracking was observed and image quality was at a level of being barely noticed, 3: Cracking was observed and slight image defects were confirmed, which was still at a level of being acceptable in practice, 2: Cracking was observed and an apparent image defect was confirmed, which was at a level to cause problems in practice.

1: A large number of cracks were observed and many image defects were noted, which were at a level to cause problems in practice.

Evaluation of Sharpness:

The radiation incident side of a flat panel detector was exposed to X-rays at a tube voltage of 40 kVp through a lead MTF chart, and the image data was detected and recorded on a hard disc. Then, the record on the hard disc was analyzed by a computer to determine a modulation transfer function, MTF (that is an MTF value at a spatial frequency cycle of 1/mm), which was a measure of sharpness. In the Table, a higher MTF value indicates superior sharpness. "MTF" is the abbreviation for Modulation Transfer Function.

The obtained MTF, which was represented by a relative value, based on the MTF value of Example 12 being 100, is shown in Table 1.

Evaluation of Luminance:

To evaluate X-ray efficiency, there was conducted luminance evaluation. The radiation incident side of a flat panel detector was exposed to X-rays at a tube voltage of 40 kVp and the image data was detected and recorded on a hard disc. Then, the record on the hard disc was analyzed by a computer and the average signal value of an X-ray image recorded on the hard disc was defined as the emission luminance. The obtained luminance, which was represented by a relative value, based on the luminance value of Example 13 being 100, is shown in Table 1.

geous in processing when coupled to various sensors such as CCD, CMOS, TFT and the like.

Description of Numeral

1 Flat panel detector
11 Planar light receiving element
12 Scintillator panel
13 Adhesive layer
14 Housing
31 Laser cutting device
32 Support board
34 Discharge tube
35 Translucent window
111 Signal extraction section
121 Support
122 Phosphor Layer
123 Protective Layer
961 Vapor deposition apparatus
962 Evacuation vessel
963 Boat
964 Holder
965 Rotation mechanism
966 Vacuum pump
S Laser-cut portion

TABLE 1

| | Constitution of Scintillator Panel | | | | Coupling with | Evaluation of Flat Panel Detector | | | |
|---|---|---|---|---|---|---|---|---|---|
| | Difference in Void Fraction between Base Portion and Edge Portion (%) | Change in Void Fraction of Base Portion (%) | Support | Protective Layer | Light Receiving Element | Shock Resistance | Bending Resistance | Sharpness (relative value) | Luminance (relative value) |
| Comparison 1 | 3 | 0.5 | C-1 | Pa | adhesive | 2 | — | 85 | 79 |
| Example 1 | 5 | 1 | C-1 | Pa | adhesive | 3 | — | 86 | 85 |
| Example 2 | 8 | 4 | C-1 | Pa | adhesive | 3 | — | 88 | 89 |
| Example 3 | 20 | 10 | C-1 | Pa | adhesive | 4 | — | 95 | 92 |
| Example 4 | 25 | 10 | C-1 | Pa | adhesive | 4 | — | 96 | 90 |
| Example 5 | 23 | 20 | C-2 | Pa | adhesive | 4 | — | 96 | 88 |
| Example 6 | 20 | 17 | C-3 | Pa | adhesive | 4 | — | 94 | 83 |
| Example 7 | 24 | 22 | A-2 | Pa | adhesive | 3 | — | 95 | 92 |
| Comparison 2 | 3 | 0.5 | P-2 | Pa | adhesive | 2 | 1 | 78 | 75 |
| Example 8 | 5 | 1 | P-2 | Pa | adhesive | 4 | 3 | 88 | 88 |
| Example 9 | 25 | 10 | P-2 | Pa | adhesive | 4 | 5 | 98 | 95 |
| Example 10 | 24 | 20 | P-2 | Pa | adhesive | 5 | 5 | 98 | 99 |
| Example 11 | 24 | 20 | P-2 | Pa | sponge | 5 | 5 | 99 | 99 |
| Example 12 | 24 | 20 | P-2 | BR | adhesive | 4 | 5 | 100 | 97 |
| Example 13 | 25 | 25 | P-2 | Pa | adhesive | 4 | 5 | 99 | 100 |
| Comparison 3 | 30 | 10 | P-2 | Pa | sponge | 1 | 2 | 95 | 94 |
| Comparison 4 | 30 | 10 | P-2 | Pa | adhesive | 1 | 2 | 93 | 93 |
| Comparison 5 | 30 | 10 | P-2 | BR | adhesive | 1 | 2 | 96 | 91 |
| Example 14 | 23 | 20 | P-3 | Pa | adhesive | 5 | 5 | 95 | 85 |
| Example 15 | 24 | 22 | A-1 | Pa | adhesive | 4 | — | 98 | 94 |
| Example 16 | 24 | 20 | P-1 | Pa | adhesive | 4 | — | 99 | 98 |
| Comparison 6 | 30 | 10 | C-1 | Pa | adhesive | 2 | — | 96 | 85 |
| Comparison 7 | 30 | 28 | C-1 | Pa | adhesive | 1 | — | 86 | 86 |

As is apparent from Table 1, it was proved that flat panel detectors of the invention each exhibited enhanced shock resistance and enhanced luminance. It was also proved that, when the change in void fraction of the base portion fell within a range of 10 to 25%, further enhanced sharpness and luminance were achieved. It was further proved that, when using a resin support which was advantageous in production efficiency, the use of a phosphor layer of the invention resulted in enhanced bending resistance, which was advanta-

What is claimed is:

1. A flat panel detector comprising a scintillator panel provided on a support with a phosphor layer comprising columnar crystals and a protective layer sequentially in this order, and the scintillator panel being coupled with a light receiving surface of a planar light receiving element having plural picture elements which are arranged two-dimensionally, wherein a difference that deducts an average void fraction of an edge portion of the phosphor layer from an average void fraction of a base portion is not less than 5% and not more than 25%, and a void fraction decreases from the base portion to the edge portion.

2. The flat panel detector, as claimed in claim 1, wherein a change in void fraction of the base portion of the phosphor layer is not less than 10% and not more than 25%.

3. The flat panel detector, as claimed in claim 1, wherein the support comprises carbon, aluminum or glass as a main component.

4. The flat panel detector, as claimed in claim 3, wherein the support exhibits a thickness of not less than 0.3 mm and not more than 1.0 mm.

5. The flat panel detector, as claimed in claim 1, wherein the support is a resin.

6. The flat panel detector, as claimed in claim 5, wherein the support comprises at least one of a polyimide (PI) and a polyethylene naphthalate (PEN).

7. The flat panel detector, as claimed in claim 5, wherein the support exhibits a thickness of not less than 0.05 mm and not more than 0.20 mm.

8. The flat panel detector, as claimed in claim 1, wherein the protective layer is a laminated film and does not adhere to the phosphor layer.

9. The flat panel detector, as claimed in claim 8, wherein the protective layer is a poly(p-xylylene) or a hot melt resin.

10. The flat panel detector, as claimed in claim 1, wherein the protective layer is a resin and adheres to the phosphor layer.

11. The flat panel detector, as claimed in claim 1, wherein the scintillator panel is coupled with the light-receiving surface of the flat light-receiving element, while pressed with an auxiliary material.

12. The flat panel detector, as claimed in claim 1, wherein the scintillator panel is coupled with the light-receiving surface of the flat light-receiving element through a resin layer.

13. The flat panel detector, as claimed in claim 1, wherein an FOP (fiber optic plate) is used for coupling of the scintillator panel with the light receiving surface of the flat light-receiving element.

14. The flat panel detector, as described in claim 1, wherein the phosphor layer comprises CsI (cesium iodide).

15. The flat panel detector, as claimed in claim 14, wherein the flat light-receiving element is a flat plate light receiving element provided with a thin film transistor (TFT) formed on a glass support.

16. The flat panel detector, as claimed in claim 14, wherein the flat light-receiving element is a CCD or a CMOS.

* * * * *